US007288373B2

(12) United States Patent
Millar et al.

(10) Patent No.: US 7,288,373 B2
(45) Date of Patent: Oct. 30, 2007

(54) TREATMENT OF METHYLATED NUCLEIC ACID

(75) Inventors: Douglas Spencer Millar, New South Wales (AU); Cassandra Jean Vockler, New South Wales (AU); Neralie Ann Coulston, New South Wales (AU)

(73) Assignee: Human Genetic Signatures Pty Ltd., New South Wales (AU)

( * ) Notice: Subject to any disclaimer, the term of this patent is extended or adjusted under 35 U.S.C. 154(b) by 493 days.

(21) Appl. No.: 10/428,310

(22) Filed: May 2, 2003

(65) Prior Publication Data

US 2004/0219539 A1 Nov. 4, 2004

(51) Int. Cl.
*C12Q 1/68* (2006.01)
*C12P 19/34* (2006.01)
(52) U.S. Cl. .......................................... 435/6; 435/91.2
(58) Field of Classification Search ...................... None
See application file for complete search history.

(56) References Cited

U.S. PATENT DOCUMENTS

| 5,786,146 A | 7/1998 | Herman et al. |
|---|---|---|
| 6,265,171 B1 | 7/2001 | Herman et al. |
| 6,331,393 B1 | 12/2001 | Laird et al. |
| 2002/0086324 A1 | 7/2002 | Laird et al. |
| 2005/0019762 A1* | 1/2005 | Olek ............................ 435/6 |

FOREIGN PATENT DOCUMENTS

| WO | WO 02/38801 | 5/2002 |
|---|---|---|
| WO | WO 02/46452 | * 6/2002 |
| WO | WO 02/72880 | 9/2002 |
| WO | WO 02/072880 | 9/2002 |

OTHER PUBLICATIONS

Tohgi et al (Molecular Brain Research (1999) 65:124-128).*
Raizis et al (Anal. Biochem. (1995) 226:161-166).*
Robertson et al (Blood (1997) 90:4480-4484).*
Clark et al., "High sensitivity mapping of methylated cytosines," *Nuc. Acids Res.* 22(15):2990-2997 (1994).
Frommer et al., "A genomic sequencing protocol that yields a positive display of 5-methylcytosine residues in individual DNA strands," *Proc. Natl. Acad. Sci.* 89:1827-1831 (1992).
Grunau et al., "Bisulfite genomic sequencing: systematic investigation of critical experimental parameters," Nucleic Acids Res. 29(13):e65-5 (2001).
International Human Genome Sequencing Consortium, "Initial sequencing and analysis of the human genome," *Nature* 409(6822):860-921 (2001).
Millar et al., "A distinct sequence (ATAAA)n separates methylated and unmethylated domains at the 5'-end of the GSTPI CpG island," *J. Biol. Chem.* 275(32):24893-24899 (2000).
Millar et al., "Detailed methylation analysis of the glutathione S-transferase pi (GSTPI) gene in prostate cancer," *Oncogene* 18(6):1313-1324.

Shapiro et al., "Deamination of cytosine derivatives by bisulfite. Mechanism of the reaction," *J. Am. Chem. Soc.* 96:206-212 (1974).
Venter et al., "The sequence of the human genome," *Science* 292(5523):1304-1351.
Database Accession No. M24485.
Grunau, et al. "Bisulfite genomic sequencing: systematic investigation of critical experimental parameters." Nucleic Acids Research, (2001), vol. 29, No. 13e65. pp. 1-7.
Clark, et al. "Bisulphite genomic sequencing of methylated cytosines." Laboratory Methods for the Detection of Mutations and Polymorphisms in DNA. Graham R. Taylor, Ed. CRC Press, New York (1997). pp. 151-162.
Venter et al., "The sequence of the human genome," *Science* 292(5523):1304-1351 (2001).
Database Accession No. M24485 (1994).
Millar et al., "Detailed methylation analysis of the glutathione S-transferase pi (GSTPI) gene in prostate cancer," *Oncogene* 18(6):1313-1324 (1999).
Xiong, et al. "COBRA: a sensitive and quantitative DNA methylation assay." (1997) Nucleic Acids Research, 25 (12): 2532-2534.
Olek, et al. "A modified and improved method for bisulphate based cystosine methylation analysis." (1996) Nucleic Acids Research, 24(24): 5064-5066.
Herman, et al. "Methylation-specific PCR: a novel PCR assay for methylation status of CpG islands." (1996) Proc. Natl. Acad. Sci. 93: 9821-9826.
Feil, et al. "Methylation analysis on individual chromosomes: improved protocol for bisulphate genomic sequencing." (1994) Nucleic Acids Research 22(4): 695-696.
Okada, et al. "Sequence Determination of Rat U5 RNA Using a Chemical Modification Procedure for Counteracting Sequence Compression." (1982) J. Biochem. 91: 1281-1291.
Specification and Preliminary Amendment from co-pending U.S. Appl. No. 10/555,465 filed Aug. 28, 2006.

* cited by examiner

*Primary Examiner*—Jeffrey Fredman
(74) *Attorney, Agent, or Firm*—Knobbe, Martens, Olson and Bear, LLP.

(57) ABSTRACT

The invention provides methods for treating methylated nucleic acids. In one embodiment, the method can include the steps of (a) providing an alkali environment to a nucleic acid sample; (b) reacting the nucleic acid sample with a bisulphite reagent and incubating the reaction so as to form a treated nucleic acid sample where methylated nucleotides in the nucleic acid sample remain unchanged while unmethylated nucleotides are converted to another form; (c) diluting the treated nucleic acid sample so as to reduce salt concentration to a level which will not substantially interfere with a nucleic acid precipitating step; (d) precipitating the diluted treated nucleic acid to substantially remove any unwanted reagents or diluents from treated nucleic acid; and (e) carrying out de-sulphonation of the precipitated treated nucleic acid so as to remove sulphonate groups present on the treated nucleic acid so as to obtain a nucleic acid sample substantially free of sulphonate groups.

30 Claims, 1 Drawing Sheet

HGS method verus traditional bisulphite method (Clark et al 1994)

1. DNA extracted from 2 LNCaP cells and treated with bisulphite
2. DNA extracted from 20 LNCaP cells and treated with bisulphite
3. DNA extracted from 200 LNCaP cells and treated with bisulphite
4. DNA extracted from 2,000 LNCaP cells and treated with bisulphite
5. DNA extracted from 20,000 LNCaP cells and treated with bisulphite

FIGURE 1

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: primer

<400> SEQUENCE: 1
tttgttgttt gtttattttt taggttt                27

<210> SEQ ID NO 2
<211> LENGTH: 26
<212> TYPE: DNA

-continued

```
<213> ORGANISM: Artificial Sequence
<220> FEATURE:
<223> OTHER INFORMATION: primer

<400> SEQUENCE: 2
aacctaatac taccaattaa ccccat                                        26

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
gggatttggg aaagagggaa aggtttttt                                     29

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
actaaaaact ctaaaaaccc catccc                                        26
```

TREATMENT OF METHYLATED NUCLEIC ACID

TECHNICAL FIELD

The present invention relates to modified methods for treating nucleic acid using bisulphite.

BACKGROUND

As a result of advances in automated sequencing technology, much work has been carried out on determining coding regions of DNA resulting in the full sequencing of many animal genomes including the human genome. It has been realised for many years that the majority of genomic DNA, however, is non-coding and this material was once considered as "junk" DNA. Analysis of the non-coding regions of DNA is now being considered as important in the study of gene expression and function. Methylation states or patterns in nucleic acid, particularly genomic DNA, is thought to have a functional or regulatory role in gene expression and control in animals.

It has been demonstrated that, in single stranded DNA, sodium bisulphite preferentially deaminates cytosine to uracil, compared to a very slow rate of deamination of 5-methylcytosine to thymine (Shapiro, R., DiFate, V., and Welcher, M, (1974) J. Am. Chem. Soc. 96: 906-912). This observation served as the basis for the development of the bisulphite genomic sequencing protocol of Frommer et al 1992 [Frommer M, McDonald L E, Millar D S, Collis C M, Watt F, Grigg G W, Molloy P L and Paul C L. PNAS 89: 1827-1831 (1992), which is incorporated herein by reference]. In summary, this method as presently practiced involves the following general steps: alkaline denaturation of DNA; deamination using sodium bisulphite; desulphonation by desalting followed by sodium hydroxide treatment; neutralization and desalting.

One of the major disadvantages of the bisulphite modification procedure and the established variation thereof is that it has been shown that the procedure results in the degradation of between 84-96% of the original input DNA (Grunau et al. Nucleic Acids Research 29 (13) e65;(2001). The high loss associated with the procedure means that practically it is very difficult to successfully analyse small numbers of cells for their methylation status, or successfully analyse ancient archival specimens in which the DNA is already in a partially degraded state. In addition, due to inherent degradation of the current methods, it is not possible to sequence and assemble the complete genome of an organism to determine its genome-wide methylation profile in the same manner as has been successfully applied by the public Human Genome Project (International Human Genome Sequencing Consortium, 2001, Nature, 409, 860-921) or the private CELERA sequencing project (J Craig Venter et al., 2001, Science, 291, 1304-1351) as the DNA would be so fragmented as it would not be able to be cloned, sequenced, and assembled in any meaningful way owing to the huge number of "gaps" in the sequence.

A further disadvantage with the bisulphite method as presently practiced is that, in general, only small fragments of DNA can be amplified. Experience shows that generally less than about 500 base pairs (bp) can be successfully treated and amplified. The present technique is not applicable to new molecular biological methods such as Long Distance polymerase chain reaction (PCR) which has made it possible to amplify large regions of untreated genomic DNA, generally up to about 50 kb. At present, it is not even possible to analyse the methylation status of intact genes, as a large number of genes in mammalian genomes exceed 50 kb in length.

To look at the methylation status of even relatively small genes (<4 kb), PCR reactions have had to be staggered across the gene region of interest (D. S Millar, K. K Ow, C. L. Paul, P. J. Russell, P. L. Molloy, S. J. Clark, 1999, *Oncogene*, 18(6):1313-24; Millar D S, Paul C L, Molloy P L, Clark S J. (2000). J Biol Chem; 275(32):24893-9). The methods presently used for bisulphite DNA treatment have also been laborious and time consuming. Standard methods typically require multiple tube changes, column purifications, dialysis, embedding the DNA in agarose beads or the addition of additives to the reaction in an attempt to reduce problems such as non-conversion of certain regions of genomic DNA. Thus a more reliable method that does not lead to substantial DNA degradation, and which overcomes or at least reduces the multiple problems associated with present DNA treatment, is required.

SUMMARY OF INVENTION

The invention relates to an improved bisulphite treatment method of nucleic acids which is efficient, adaptable for use with many different molecular biological techniques, and can achieve significant retention of nucleic acid, which is herein termed the HGS method or invention.

The invention provides, in one embodiment, a method for treating methylated nucleic acids. The method can include the steps of denaturing a nucleic acid sample; incubating the nucleic acid sample with a bisulphite reagent, thereby modifying methylated nucleotides with sulphonate groups; diluting the modified nucleic acid sample; precipitating the modified nucleic acid sample; and reacting the modified nucleic acid sample to remove sulphonate groups. The denaturation of the nucleic acid can be performed, for example, by treatment with alkali.

In another embodiment, the present invention provides a method for treating methylated nucleic acid comprising:

(a) providing an alkali environment to a nucleic acid sample;

(b) reacting the nucleic acid sample with a bisulphite reagent and incubating the reaction so as to form a treated nucleic acid sample where any methylated nucleotides in the nucleic acid sample remain unchanged while unmethylated nucleotides are converted to another form;

(c) diluting the treated nucleic acid sample so as to reduce salt concentration to a level which will not substantially interfere with a nucleic acid precipitation step;

(d) precipitating the diluted treated nucleic acid to substantially remove any unwanted reagents or diluents from the vessel; and (e) carrying out de-sulphonation of the precipitated treated nucleic acid so as to remove sulphonate groups present on the treated nucleic acid so as to obtain a nucleic acid sample substantially free of sulphonate groups without inducing significant amounts of strand breakage.

The method typically retains more than about 50%, generally more than about 75%, and can be more than about 95% of the starting nucleic acid in the sample. The methods of the invention can be carried out without causing any substantial degradation or loss of the nucleic acid sample. In contrast, bisulphite methods presently in use or described in the prior art typically result in loss of up to about 96% of the nucleic acid sample so that only about 4% of the nucleic acid is actually available for analysis.

The method may further comprise:
(f) further processing or analysing the treated nucleic acid sample.

The sample may include DNA or RNA or a combination of both DNA and RNA.

Unlike prior art methods, there is no need to completely separate or isolate the treated nucleic acid from the bisulphite reagent. There is no need to employ chromatography separation methods, for example, as presently required by prior art methods. The dilution step according to the present invention assists in minimizing loss of sample.

These and other features of the invention will be appreciated from review of the following detailed description of the invention along with the accompanying figures.

DETAILED DESCRIPTION OF INVENTION

Embodiments for treating methylated nucleic acid are described in non-limiting detail below.

The invention provides methods for the treatment and analysis of methylated nucleic acids. The methods are advantageous in that they provide a simple and highly efficient method for modification of methylated nucleic acids and can be used, for example, to examine the methylation pattern or changes in methylation of genomic DNA. The methods of the invention provide a simplified procedure with higher yields and higher molecular weight DNA relative to previously known methods, thus allowing the analysis of smaller amounts of methylated nucleic acids as well as easy application to a large number of samples.

The invention provides a method for treating methylated nucleic acid comprising:
(a) denaturing a nucleic acid sample;
(b) reacting the nucleic acid sample with a bisulphite reagent and incubating the reaction so as to form a treated nucleic acid sample where any methylated nucleotides in the nucleic acid sample remain unchanged while unmethylated nucleotides are converted to another form;
(c) diluting the treated nucleic acid sample so as to reduce salt concentration to a level which will not substantially interfere with a nucleic acid precipitation step;
(d) precipitating the diluted treated nucleic acid to substantially remove any unwanted reagents or diluents from treated nucleic acid sample; and
(e) carrying out de-sulphonation of the precipitated treated nucleic acid so as to remove sulphonate groups present on the treated nucleic acid so as to obtain a nucleic acid sample substantially free of sulphonate groups.

The denaturation of the nucleic acid sample can be performed, for example, by providing an alkali environment to the sample. The methods are particularly useful in the analysis of DNA nucleic acid samples. The desulphonation step is generally carried out under controlled conditions so as to remove sulphonate groups present on the treated nucleic acid sample. The methods are advantageous because they can be performed so that the nucleic acid sample, for example, strands of DNA, are not broken or sheared to a significant extent.

The invention thus provides, in one embodiment, a method for treating methylated nucleic acids. The method can include the steps of denaturing a nucleic acid sample; incubating the nucleic acid sample with a bisulphite reagent, thereby modifying methylated nucleotides with sulphonate groups; diluting the modified nucleic acid sample; precipitating the modified nucleic acid sample; and reacting the modified nucleic acid sample to remove sulphonate groups. The denaturation of the nucleic acid can be performed, for example, by treatment with alkali.

The method typically results in more than about 50%, generally more than about 75%, and can result in more than about 95% of the starting nucleic acid in the sample being retained. The present inventors have found that the method can be carried out without causing any substantial degradation or loss of the nucleic acid sample. In contrast, bisulphite methods presently in use or described in the prior art typically result in loss of up to about 96% of the nucleic acid sample.

The method may further comprise:
(f) further processing or analysing the treated nucleic acid sample.

The sample may include DNA or RNA or a combination of both DNA and RNA.

The sample can be prepared from tissue, cells or can be any biological sample such as blood, urine, faeces, semen, cerebrospinal fluid, lavage, cells or tissue from sources such as brain, colon, urogenital, lung, renal, hematopoietic, breast, thymus, testis, ovary, uterus, tissues from embryonic or extra-embryonic linages, environmental samples, plants, microorganisms including bacteria, intracellular parasites virus, fungi, protozoan, viroid and the like. The best described mammalian cell types suitable for treatment by the present invention are summarized in B. Alberts et al., 1989, The Molecular Biology of the Cell, $2^{nd}$ Edition, Garland Publishing Inc New York and London, pp 995-997.

The analysis of 5-methyl cytosine residues in DNA from samples of human, animal, plant, bacterial, and viral origin is meant to cover all life cycle stages, in all cells, tissues and organs from fertilization until 48 hours post mortem, as well as samples that may be derived from histological sources, such as microscope slides, samples embedded in blocks, or samples extracted from synthetic or natural surfaces or from liquids.

The analyses are meant to include the naturally occurring variation between cells, tissues and organs of healthy individuals, (health as defined by the WHO), as well as cells, tissues and organs from diseased individuals. Diseased in this sense includes all human diseases, afflictions, ailments and deviant conditions described or referred to in Harrison's Principles of Internal Medicine, 12th Edition, edited by Jean D Wilson et al., McGrraw Hill Inc, and subsequent later editions; as well as all diseases, afflictions ailments and deviant conditions described in OMIM (Online Mendelian Inheritance in Man, www.ncbi.gov), but with emphases on the leading causes of death, namely, malignant neoplasms, (cancer), ischaemic heart disease, cerebrovascular disease, chronic obstructive pulmonary disease, pneumonia and influenza, diseases of arteries, (including atherosclerosis and aortic aneurysm), diabetes mellitus, and central nervous system diseases, together with socially debilitating conditions such as anxiety, stress related neuropsychiatric conditions and obesity, and all conditions arising from abnormal chromosome number or chromosome rearrangements, (aneuploidy involving autosomes as well as sex chromosomes, duplications, deficiencies, translocations and insertions), as well as similar abnormalities of the mitochondrial genomes.

The normal or diseased individuals may be from (i) populations of diverse ethnicity and evolutionary lineages; (ii) strains and geographical isolates; (iii) sub species; (iv) twins or higher order multiplets of the same or different sex; (v) individuals arising from normal methods of conjugation, artificial insemination, cloning by embryonic stem cell methods, or by nuclear transfer, (from somatic or germ line nuclei), or from the input or modification of mitochondrial or other cellular organelles; (vi) individuals deriving from transgenic knock-out, knock-in or knock-down methods, (either in vivo, ex vivo, or by any method in which gene activity is transiently or permanently altered, e.g., by RNAi, ribozyme, transposon activation, drug or small molecule methodologies, Peptide Nucleic Acid (PNA), Intercalating Nucleic Acid (INA), Altritol Nucleic Acid (ANA), Hexitol Nucleic Acid (HNA), Locked Nucleic Acid (LNA), Cyclohexanyl Nucleic Acid (CNA), and the like, or nucleic acid based conjugates, including but not restricted to Trojan peptides, or individuals at any stages of pregnancy, normal or ectopic.

The analyses also include 5-methyl cytosine residues in DNA from prokaryotic or eukaryotic organisms and viruses (or combinations thereof), that are associated with human diseases in extracellular or intracellular modes, for the purposes of determining, and therapeutically altering, in both normally varying and diseased systems, the changed parameters and underlying mechanisms of:

(i) genetic diseases;
(ii) non-genetic or epigenetic diseases caused by environmentally induced factors, be they of biological or non-biological origin, (environmental in this sense being taken to also include the environment within the organism itself, during all stages of pregnancy, or under conditions of fertility and infertility treatments);
(iii) predisposition to genetic or non genetic diseases, including effects brought about by the "prion" class of factors, by exposure to pressure changes and weightlessness, or by radiation effects;
(iv) 5-methyl cytosine changes in the processes of aging in all cell types, tissues, organ systems and biological networks, including age related depression, pain, neuropsychiatric and neurodegenerative conditions and pre- and post-menopausal conditions, (including reduced fertility; in both sexes);
(v) 5-methyl cytosine changes in cancer, (including changes in cells with abnormal karyotypes arising from DNA amplification, deletion, rearrangement, translocation and insertion events), and their variations or alterations in different cell cycle phenomena (including cell cycle effects on diurnal rhythms, photoperiod, sleep, memory, and "jet lag";
(vi) 5-methyl cytosine changes in metabolic networks defined in the broadest sense, from the zygote through embryogenesis, foetal development, birth, adolescence, adulthood and old age (including metabolic effects brought about by hypoxia, anoxia, radiation of any type, (be it ionizing or non ionizing, or arising from chemotherapeutic treatments, high altitude exposure radiation from nearby natural sources, such as rocks or from "fallout" from military or government sponsored activities), stress, or by imbalances between the mitochondrial, nuclear or organellar genomes;
(vii) 5-methyl cytosine alterations due to responses at the molecular, cellular, tissue, organ and whole organism levels to proteins, polypeptides, peptides, and DNA, RNA, PNA, INA, ANA, HNA, LNA, CNA, and the like, or peptide aptamers (including any with post translational additions, post translational cleavage products, post translational modifications (such as inteins and exeins, ubiquination and degradation products); proteins, polypeptides and peptides containing rare natural amino acids, as well as single rare amino acids such as D-serine involved in learning, brain growth and cell death; drugs, biopharmaceuticals, chemical entities (where the definitions of Chemical Entities and Biopharmaceuticals is that of G. Ashton, 2001, Nature Biotechnology 19, 307-3111)), metabolites, new salts, prodrugs, esters of existing compounds, vaccines, antigens, polyketides, non-ribosomal peptides, vitamins, and molecules from any natural source (such as the plant derived cyclopamine);
(viii) 5-methyl cytosine alterations due to responses at the molecular, cellular, tissue, organ and whole organism levels to RNA and DNA viruses be they single or double stranded, from external sources, or internally activated such as in endogenous transposons or retrotransposons, (SINES and LINES);
(ix) 5-methyl cytosine alterations due to responses at the molecular, cellular, tissue, organ and whole organism levels to reverse transcribed copies of RNA transcripts be they of genic or non genic origins, (or intron containing or not);
(x) 5-methyl cytosine alterations due to responses at the molecular, cellular, tissue, organ and whole organism levels to: (a) DNA, RNA, PNA, INA, ANA, HNA, LNA, CNA, and the like (or DNA, RNA, PNA, INA, ANA, HNA, LNA, CNA, aptamers of any in all combinations); including DNA, RNA, PNA, INA, ANA, HNA, LNA, CNA, and the like molecules circulating in all fluids including blood and cerebrospinal fluid as well as maternal fluids before, during and after pregnancy (b) combinations of conjugated biomolecules that are chimeras of peptides and nucleic acids; or chimeras of natural molecules such as cholesterol moieties, hormones and nucleic acids; and
(xi) 5-methyl cytosine alterations due to responses of stem cells, (either in vivo, ex vivo or in association with novel environments or natural and synthetic substrates (or combinations thereof), from human and animal origin to any of the perturbations described in (i) to (x) above.

Any suitable method for obtaining nucleic acid material can be used. Examples include, but are not limited to, commercially available DNA, RNA kits or reagents, workstation, standard cell lysis buffers containing protease reagents and organic extraction procedures, which are well known to those of skill in the art.

The method can be carried out in a reaction vessel. The reaction vessel can be any suitable vessel such as tube, plate, capillary tube, well, centrifuge tube, microfuge tube, slide, coverslip or any suitable surface. The method is generally carried out in one reaction vessel in order to reduce the likelihood of degradation or loss of the nucleic acid sample.

Generally, the alkali environment is provided to the sample by adding an alkali such as NaOH. The alkali environment is provided to denature double stranded nucleic acid molecules into a state where the molecules are readily reactive with the bisulphite reagent. It will be appreciated, however, that any other denaturation method such as heat treatment or other suitable alkali or denaturing agent can be added or used such as KOH and any other alkali so long as use of the reagents for denaturation do not significantly inhibit subsequent steps.

Generally, the bisulphite reagent is sodium metabisulphite. The bisulphite reagent is used to cause sulphonation of cytosine bases to cytosine sulphonate followed by hydrolytic deamination of the cytosine sulphonate to uracil sulphonate. It will be appreciated, however, that any other suitable bisulphite reagent could be used such as sulphite or acetate ions (see Shapiro, R., DiFate, V., and Welcher, M, (1974) J. Am. Chem. Soc. 96: 906-912).

The incubation with the sulphonating reagent can be carried out at pH below 7 and at a temperature which favors the formation of the uracil sulphonate group. A pH below 7 is optimal for carrying out the sulphonation reaction, which converts the cytosine bases to cytosine sulphonate and subsequently to uracil sulphonate. However, the methods of the invention can be performed with the sulphonation reaction above pH 7, if desired.

The sulphonation reaction can be carried out in the presence of an additive capable of enhancing the bisulphite reaction. Examples of suitable additives include, but not limited to, quinol, urea, methoxyamine. Of these reagents, quinol is a reducing agent. Urea and methyoxyamine are agent added to improve the efficiency of the bisulphite reaction. It will be appreciated that other additives or agents can be provided to assist in the bisulphite reaction.

The sulphonation reaction results in methylated cytosines in the nucleic acid sample remaining unchanged while unmethylated cytosines are converted to uracils.

Reaction conditions found to work well are as follows. The DNA, or other nucleic acids, to be treated is made up to a volume of 20 µl. Then 208 µl of a freshly prepared solution of 2 M sodium metabisulphite (BDH AnalaR #1 0356.4D) pH 5.0 (the pH is adjusted by the addition of 10M sodium hydroxide (BDH AnalaR #10252.4X) along with 12 µl of a 10 mM quinol solution (BDH AnalaR #1031 22E). The concentration of quinol added can be anything in the range of about 10 to 500 mM as determined experimentally. The solution is then vortexed and overlayed with 208 µl of mineral oil (Sigma molecular biology grade M-5904). The sample is then left overnight at a suitable temperature, for example, room temperature or another suitable temperature, to allow time for full bisulphite conversion. It is understood by those skilled in the art that the volumes, concentrations and incubation time and temperature described above are merely exemplary and can be varied so long as the reaction conditions are suitable for sulphonation of the nucleic acids. It is also understood that the order of the steps of methods of the invention can be varied so long as the sulphonation and desulphonation steps are sufficiently carried out.

The dilution step is performed so that the salts inhibitory to subsequent reactions are not co-precipitated with the sulphonated nucleic acids. The salt concentration is diluted to less than about 1 M. Generally, the dilution step is carried out using water or buffer to reduce the salt concentration to below about 0.5M. For example, the salt concentration is generally diluted to less than about 1 mM to about 1 M, in particular, less than about 0.5 M, less than about 0.4 M, less than about 0.3 M, less than about 0.2 M, less than about 0.1 M, less than about 50 mM, less than about 20 mM, less than about 10 mM, or even less than about 1 mM, if desired. One skilled in the art can readily determine a suitable dilution that diminishes salt precipitation with the nucleic acids so that subsequent steps can be performed with minimal further clean up or manipulation of the nucleic acid sample. The dilution is generally carried out in water but can be carried out in any suitable buffer, for example Tris/EDTA or other biological buffers so long as the buffer does not precipitate significantly or cause the salt to precipitate significantly with the nucleic acids so as to inhibit subsequent reactions.

Unlike prior art methods, there is no need to completely separate or isolate the treated nucleic acid from the bisulphite reagent. There is no need to employ chromatography separation methods, for example, as presently required by prior art methods. The dilution step according to the, present invention assists in minimizing loss of sample.

Generally, precipitation is carried out using a precipitating agent such as an alcohol. An exemplary alcohol for precipitation of nucleic acids can be selected from isopropanol, ethanol or any other suitable alcohol.

The de-sulphonation step can be carried out by adjusting the pH of the precipitated treated nucleic acid up to about 12.5. Exposure to alkaline environments tends to promote strand breaks in apurinic sites in the DNA induced by the previous exposure to an acidic pH. Therefore, the alkaline pH treatment is minimized if strand breaks are to be avoided. This step can be carried out efficiently at around pH 10.5 with a suitable buffer or alkali reagent. Examples of suitable buffers or alkali reagents include buffers having a pH 7.0-12.5. It will be appreciated by persons skilled in the art that suitable buffers or alkali reagents can be selected from the vast range of known buffers and alkali reagents available.

Temperature ranges for the de-sulphonation step are room temperature to about 96° C. and times can vary from 2 minutes to 96 hours or longer depending on the conditions used. One skilled in the art can readily determine a suitable time and temperature for carrying out the de-sulphonation reaction. Temperatures below room temperature can also be used so long as the incubation time is increased to allow sufficient desulphonation. Thus, the incubation step can be carried out at about 10° C., about 20° C., about 22° C., about 25° C., about 30° C., about 35° C., about 37° C. about 40° C. about 45° C., about 50° C., about 55° C., about 60° C., about 65° C., about 70° C. about 75° C. about 80° C., about 85° C., about 90° C., about 95° C., and about 96° C., A particularly useful temperature for carrying out the desulphonation reaction is about 55° C. These and other incubation and/or reaction steps can be similarly carried out at various temperatures, as described above, so long as a sufficient reaction step is performed.

The present invention provides methods for the efficient characterization of methylated nucleic acids. The methods allow efficient sulphonation and desulphonation steps to be carried out on the nucleic acid sample. However, it is understood that neither of the sulphonation or desulphonation steps need be carried out to completion, only sufficiently to subsequently characterize methylation of the nucleic acid, as disclosed herein. One skilled in the art can readily determine whether these steps should be carried out to near completion or whether incomplete reactions are sufficient for a desired analysis. For example, when a small number of cells or a small amount of nucleic acid sample are used, it is generally desired that a more complete reaction be performed. When larger quantities of nucleic acid sample are being characterized, a less complete reaction can be carried out while still providing sufficient reaction products for subsequent analysis of the methylation state of the nucleic acid sample.

As disclosed herein, the invention provides methods for conveniently treating methylated nucleic acids. The methods can be used for the analysis of the methylation state of a genome as a measure of the state of a cell, tissue or organism, as disclosed herein. The methods of the invention provide several advantages over methods previously used for treating methylated nucleic acids. One advantage is that the method of the invention allows omission of the chromatography step that is traditionally used to desalt the nucleic acid sample after sulphonation (Clark et al., 1994). The chromatography step leads to loss of the sulphonated nucleic acid sample, which can be particularly problematic when working with small amounts of starting material.

Another advantage of the invention is that the desalting step is carried out in a highly efficient manner by diluting the salt concentration and precipitating the nucleic acids. The dilution step reduces the salt concentration below an amount that, when the nucleic acid is precipitated, does not interfere with subsequent steps such as desulphonation. The precipitation step is highly efficient and can optionally include carriers that increase the efficiency of nucleic acid precipitation. Thus, the methods of the invention minimize loss and increase recovery of nucleic acid samples. Accordingly, the methods of the invention provide the additional advantage of allowing even smaller amounts of starting material to be used and efficiently characterized with respect to methylation. The invention provides methods that improve upon the method of Clark et al., 1994, by substituting the use of a cumbersome and inefficient chromatography separation method with a simple dilution and precipitation method in the step of removing any unwanted reagents or diluents from the nucleic acids.

Further, the use of a buffer solution at slightly alkaline pH can be used to decrease the likelihood that the nucleic acid of interest becomes substantially fragmented. Increasing the pH of the buffered solution to much above pH 11 has been demonstrated to lead to very substantial fragmentation of high molecular weight nucleic acids. Therefore, when it is desired to minimize such fragmentation, an alkaline pH below pH 11 is generally used.

Yet another advantage of the invention is that the reactions can be carried out in a single tube or vessel for each sample, thus minimizing sample loss and allowing the processing of numerous samples. A further advantage of the method of the invention compared to previous methods is that the nucleic acids, once sulphonated, can be resuspended in a buffer having a basic pH to carry out the desulphonation step rather than requiring the addition of strong base and the subsequent removal of salts, as in the method describe by Clark et al., 1994.

Still another advantage is that the methods of the invention allow the optional digestion with restriction enzymes prior to treatment. The traditional bisulphite treatment method generally includes an initial digestion step with a restriction enzyme for successful treatment and amplification and is therefore not applicable to long distance PCR reactions. However, the methods of the invention do not require pre-digestion with restriction enzymes prior to the sulphonation reaction, again allowing fewer manipulations as well as the option of performing PCR on longer fragments.

The methods of the invention can be used to characterize the methylation state of a cell, tissue or organism. The methods of the invention can also be used in conjunction with genomic sequencing methods such as those described by Frommer et al., Proc. Natl. Acad. Sci. USA 89:1827-1831 (1992), which is incorporated herein by references.

The invention additionally provides a method of determining the methylation state of a sample. The method can be carried out on a sample using the method of the invention for treatment of methylated nucleic acids, that is, the HGS method. The method for determining the methylation state of a sample can be carried out in parallel with a test sample and a control sample so that the methylation state of the sample can be compared and determined relative to a reference sample. For example, the samples can be compared to determine whether there is an increase or decrease of methylation in general or at particular sites. Such a determination can be used to diagnose and/or determine the prognosis of a disease, as discussed herein. The method can further include reporting of the methylation state of a sample, for example, in a diagnostic application.

It is understood that the components of the method of the invention can be provided in the form of a kit. The kit can contain appropriate chemical reagents, reaction tubes and instructions for carrying out the method of the invention.

EXAMPLES

Methods and Reagents

Chemicals were obtained as follows: Agarose from Bio-Rad (Hercules Calif.; certified molecular biology grade #161-3101); Acetic acid, glacial, from BDH (Kylsyth, Australia; AnalaR 100015N); ethylenediamine tetraacetic acid (EDTA) from BDH (AnalaR 10093.5V); Ethanol from Aldrich (St. Louis Mo.; 200 proof E702-3); Isopropanol from Sigma (St. Louis Mo.; 99%+Sigma I-9516); Mineral oil from Sigma (M-5904); Sodium acetate solution 3M from Sigma (S-7899); Sodium chloride from Sigma (ACS reagent S9888); and Sodium hydroxide from BDH (AnalaR #10252.4X).

Enzymes/Reagents were obtained as follows: EcoR1 from Roche (Indianapolis Ind.; #87930626, 10 units/µl); HindIII from Biolabs (Beverly Mass.; #R01045, 10 units/µl); PCR master mix from Promega (Madison Wis.; #M7505); and DNA markers from Sigma (Direct load PCR low ladder 100-1000 bp, Sigma D-3687 and 100-10 Kb, Sigma D-7058).

Solutions were as follows: (1) 10 mM Tris/0.1 M EDTA, pH 7.0-12.5; (2) 3M NaOH (6 g in 50 ml water; BDH AnalaR #10252.4X); (3) 2M Metabisulphite (7.6 g in 20 ml water with 416 µl 10 N NaOH (BDH AnalaR #10356.4D); (4) 10 mM Quinol (0.055 g in 50 ml water; BDH AnalaR #103122E); (5) 50 X TAE gel electrophoresis buffer (242 g Trizma base, 57.1 ml glacial acetic acid, 37.2 g EDTA and water to 1 l); and (6) 5 X Agarose gel loading buffer (1 ml 1% Bromophenol blue (Sigma B6131), 1 ml Xylene Cyanol (Sigma X-4126), 3.2 ml Glycerol (Sigma G6279), 8 µl 10.5 M EDTA pH 8.0, 200 µl 50 X TAE buffer and water to 10 ml).

Tissues and Cell Lines

Tissues and cell lines were obtained as follows: Hela (cervical cancer cell line, ATCC CCL-2); LNCaP (prostate cancer cell line, ATCC #CRL-10995); HepG2 (liver cancer cell line, ATCC #HB-8065); and MCF-7 (breast cancer cell line, ATCC #HTB-22) were obtained from American Type Culture Collection.

For preparation of T-medium for growth of LNCaP Cells, reagents were obtained from Gibco/BRL or Invitrogen, except as indicated, as follows: DMEM powder 10× sachets (10×1 l; #31600-034); F-12K Nutrient mixture, Kaighn's Modifn. (500 ml; #21127-022); L-Glutamine, 200 mM (100 ml; #25030-081); Penicillin/Streptomycin 5000 U/ml, 5000 μg/ml (100 ml #15070-063 Thermo Trace); Foetal Bovine serum (500 ml; #15-010-0500V Sigma); Insulin (Bovine pancreas) (100 mg; #11882); Transferrin (Human) (10 mg; #T5391); d-Biotin (500 mg; #B4639); Adenine (5 g; #A3159); T3 (#T6397 or #T5516).

T-media (500 ml) was prepared as follows: DMEM stock solution was prepared by adding 3.7 g Sodium bicarbonate per liter and adjusting the pH to between 7.2-7.4. To 400 ml of DMEM stock solution, the following reagents were added: 100 ml of F-12K; 250 μl of insulin (10 mg/ml); 1.0 ml T3 (500×; Tri-iodothyronine; 6.825 ng/ml); 1.0 ml transferring (500×; 2.5 mg/ml); 1.0 ml Biotin (500×; 0.122 mg/ml); 4.0 ml Adenine (125×; 3.125 mg/ml); 5.5 ml Penicillin/Streptomycin (100×; 5000 μg/ml); and 5.5 ml Glutamine (100×; 200 mM). After sterile filtration, 50 ml of Foetal Bovine Serum was added to give 10%.

Table 1 sets out the cell lines and growing conditions used in the experiments outlined below.

TABLE 1

Cells

| NAME | Cell Type | GROWING CONDITIONS |
|---|---|---|
| BL13 | Bladder Cancer | RPM1 + 10% HI FCS Split 1:3, 2× week |
| HeLa | Cervical Carcinoma | RPM1 + 10% HI FCS for initial rapid growth then DMEM + 10% HI FCS for slower growth. Split 1:10, 2× week |
| HepG2 | Liver Carcinoma | DMEM (high glucose 4.5 g/l) + 10% HI FCS + 2 mM Glutamine. Split 1:4 2× week |
| LNCAP | Prostate Cancer (Methylated) | DMEM (low glucose) + 10% HI FCS + 2 mM Glutamine + Lots of other supplements, see LNCaP growth method sheet above. |
| MCF7 | Breast Cancer | RPM1 + 10% HI FCS Split 1:6, 2× week |

Purification of T-cells and CD34+ cells from Whole Blood

Samples were obtained from a patient undergoing leukapheresis at the Royal North Shore Hospital, Sydney. Samples were obtained with prior Ethics Committee approval. White blood cells were concentrated using Ficoll Paque plus (Amersham Biosciences #17-1440-03; Piscataway N.J.) according to the manufacturers instructions. T-cells and CD34+ cells were isolated from the white cell population using CELLection CD2 Dynabeads (Dynal #116.03; Lake Success N.Y.) and Dynal CD34 Progenitor Cell selection system (Dynal #113.01) respectively according to the manufactures instructions.

The following equipment was used: the PCR machine was ThermalHybaid PX2 (Sydney, Australia) the Gel Documentation System was a Kodak UVItec EDAS 290 (Rochester N.Y.), and the microfuge was an Eppendorf 5415-D (Brinkman Instruments; Westbury N.Y.).

DNA Amplification

PCR amplifications were performed in 25 μl reaction mixtures containing 2 μl of bisulphite-treated genomic DNA, using the Promega PCR master mix, 6 ng/μl of each of the primers. The strand-specific nested primers used for amplification of GSTP1 from bisulphite-treated DNA are GST-9 (967-993) TTTGTTGTTTGTTTATTTTTTAGGTTT (SEQ ID NO:1) (F) GST-10 (1307-1332) AACCTAATAC-TACCAATTAACCCCAT (SEQ ID NO:2) (R) GST-11 (999-1027) GGGATTTGGGAAAGAGGGAAAGGTTTTT (SEQ ID NO:3) (F) GST-12 (1281-1306) ACT-AAAAACTCTAAAAACCCCATCCC (SEQ ID NO:4) (R). The location of the primers is indicted according to the GSTP1 sequence (Accession number: M24485; GenBank citation Morrow et al., Gene 75:3-11 (1989)).

DNA Separation

1% or 2% agarose gels were prepared in 1% TAE containing 1 drop ethidium bromide (CLP #5450) per 50 ml of agarose. The DNA sample of interest (genomic or PCR derived) was mixed with $\frac{1}{5}^{th}$ volume 5× agarose loading buffer and electrophoresed at 125 mA in X1 TAE using a submarine horizontal electrophoresis tank.

Traditional Bisulphite Treatment of DNA (Clark et al., (1994) Nucleic Acids Res. 22:2990-2997, which is incorporated herein by reference)

Genomic DNA (2 μg) was digested with Eco R1 for 60 minutes at least in a final volume of 20 μl. To this digest, 2.2 μl of 3M NaOH (6 g NaOH/50 ml water, made fresh) were added and incubated at 37° C. for 15 minutes. A 208 μl volume of 2M Metabisulphite (7.6 g metabisulphite/20 ml water and 416 μl 10M NaOH to pH 5.0) was added followed by 12 μl of 10 mM quinone (0.55 g hydroquinone gives 100 mM, dliute 1/10). The reaction mixture was overlaid with 200 μl of mineral oil and incubated at 50-55° C. overnight. At the end of the incubation, the mineral oil was removed and 1 μg yeast tRNA (Sigma R-8508) was added.

DNA desalting was carried out using the Wizard DNA clean up system (Promega #A7280) according to the manufactures instructions. Briefly, 1 ml of resin was added to the sample and the sample vortexed. The sample was applied to a column attached to a 2.5 ml syringe and pushed through the syringe gently. The column was washed with 2 ml of 80% isopropanol and then spun for 20 seconds at 14,000 rpm in a microfuge. Fifty μl of water was applied to the column and the sample left for 1 minute at room temperature. The column material was applied to a clean 1.5 ml centrifuge tube and was spun for 20 seconds at 14,000 rpm in a microfuge. The DNA was recovered in the eluted volume, ready for de-sulphonation.

To remove the sulphate groups from uracil, 5.5 μl of 3M NaOH were added to the eluted DNA and the mixture was incubated at 37° C. for 15 minutes. A 33.5 μl volume of NH$_4$OAC (pH 7.0) was added to neutralize the alkali. A 330 μl of 100% ethanol was added, and the reaction mixture was incubated at −20° C. for 60 minutes. The sample was spun 15 minutes at 14,000 rpm and the ethanol was discarded. The pellet was air dried and resuspended in 10 μl T/E (pH 8.0).

Bisulphite Treatment of DNA according to the Present Invention

An exemplary protocol demonstrating the effectiveness of the bisulphite treatment according to the present invention is set out below. The protocol successfully resulted in retaining substantially all DNA treated. This method of the invention is also referred to herein as the Human Genetic Signatures (HGS) method. It will be appreciated that the volumes or amounts of sample or reagents can be varied.

To 2 μg of DNA, which can be pre-digested with suitable restriction enzymes if so desired, 2 μl (1/10 volume) of 3 M NaOH (6 g in 50 ml water, freshly made) was added in a final volume of 20 μl. This step denatures the double stranded DNA molecules into a single stranded form, since the bisulphite reagent preferably reacts with single stranded molecules. The mixture was incubated at 37° C. for 15 minutes. Incubation at temperatures above room temperature can be used to improve the efficiency of denaturation.

After the incubation, 208 µl 2 M Sodium Metabisulphite (7.6 g in 20 ml water with 416 ml 10 N NaOH; BDH AnalaR #10356.4D; freshly made) and 12 µl of 10 mM Quinol (0.055 g in 50 ml water, BDH AnalR #103122E; freshly made) were added in succession. Quinol is a reducing agent and helps to reduce oxidation of the reagents. Other reducing agents can also be used, for example, dithiothreitol (DTT), mercaptoethanol, quinone (hydroquinone), or other suitable reducing agents. The sample was overlaid with 200 µl of mineral oil. The overlaying of mineral oil prevents evaporation and oxidation of the reagents but is not essential. The sample was then incubated overnight at 55° C. Alternatively the samples can be cycled in a thermal cycler as follows: incubate for about 4 hours or overnight as follows: Step 1, 55° C./2 hr cycled in PCR machine; Step 2, 95° C./2 min. Step 1 can be performed at any temperature from about 37° C. to about 90° C. and can vary in length from 5 minutes to 8 hours. Step 2 can be performed at any temperature from about 70° C. to about 99° C. and can vary in length from about 1 second to 60 minutes, or longer.

After the treatment with Sodium Metabisulphite, the oil was removed, and 1 µl tRNA (20 mg/ml) or 2 µl glycogen were added if the DNA concentration was low. These additives are optional and can be used to improve the yield of DNA obtained by co-precitpitating with the target DNA especially when the DNA is present at low concentrations. The use of additives as carrier for more efficient precipitation of nucleic acids is generally desired when the amount nucleic acid is <0.5 µg.

An isopropanol cleanup treatment was performed as follows: 800 µl of water were added to the sample, mixed and then 1 ml isopropanol was added. The water or buffer reduces the concentration of the bisulphite salt in the reaction vessel to a level at which the salt will not precipitate along with the target nucleic acid of interest. The dilution is generally about ¼ to ¹⁄₁₀₀₀ so long as the salt concentration is diluted below a desired range, as disclosed herein.

The sample was mixed again and left at −20° C. for a minimum of 5 minutes. The sample was spun in a microfuge for 10-15 minutes and the pellet was washed 2× with 80% ETOH, vortexing each time. This washing treatment removes any residual salts that precipitated with the nucleic acids.

The pellet was allowed to dry and then resuspended in a suitable volume of T/E (10 mM Tris/0.1 mM EDTA) pH 7.0-12.5 such as 50 µl. Buffer at pH 10.5 has been found to be particularly effective. The sample was incubated at 37° C. to 95° C. for 1 min to 96 hr, as needed to suspend the nucleic acids.

The method described above can be preceded by digestion with one or more restriction enzymes. Two independent restriction enzyme digests are set up of the same sample of DNA as described below. The enzymes selected for digestion are dependent upon the sequence to be amplified. For example, digest 2 µg genomic DNA with EcoRI in a 20 µl volume for 1 hr/at 37° C. This step is used to digest the genomic DNA into smaller fragments which are more amenable to bisulphite conversion than genomic DNA. Sonication or physical forces can also be used to shear the DNA into smaller sized fragments. The intensity of sonication and the length of sonication is selected based on the desired size of DNA fragments. A separate digestion reaction is carried out, for example, by digesting 2 µg genomic DNA with HindIII as described above. These or other suitable restriction enzymes can be selected for pretreatment digestion. The digested DNA is treated with metabisulfite as described above.

Analysis of LNCaP Cells and Sensitivity of PCR Amplification

Cultures of LNCaP cells were grown under standard conditions to 90% confluence. Cells were trypsinised, washed, then counted using a haemocytometer. Cells were then diluted to contain the approximate number of cells as indicated in Table 2. The cells were then lysed using MasterPure DNA Purification kit (Epicentre #MCD85201; Madison Wis.) as described by the manufacturers instructions and the DNA then modified using the two sulphonation methods described above.

After accurate determination of cell numbers, cells were split in duplicate into 1.5 ml eppendorf centrifuge tubes at the following cell numbers 100, 1000, 10000 and 100000 in 25 µl of T/E pH 8.0. Cell lysis was then performed on the cells as described by the manufacture's instructions MasterPure DNA Purification kit (Epicentre #MCD85201) as described by the manufacturers instructions.

DNA was resuspended in 10 µl of T/E pH 8.0. DNA was then digested with 1 unit of EcoR1 (Roche #87930626 10 units/µl) according to the manufacturers instructions for 1 hour at 37° C. in a final volume of 20 µl.

Traditional bisulphite treatment of DNA (Clark et al 1994) was performed on one set of duplicates while the HGS bisulphite treatment of DNA was performed on the other set. After treatment DNA was resuspended in 5 µl of T/E pH 8.0.

PCR amplification was performed on 1 µl of treated DNA, $\frac{1}{5}^{th}$ volume of final resuspended sample volume, as follows. PCR amplifications were performed in 25 µl reaction mixtures containing 1 µl of bisulphite-treated genomic DNA, using the Promega PCR master mix, 6 ng/µl of each of the primers. The strand-specific nested primers used for amplification of GSTP1 from bisulphite-treated DNA are GST-9 (967-993) TTTGTTGTTTGTTTATTTTTTAGGTTT (SEQ ID NO:1) (F) GST-10 (1307-1332) AACCTAATACTAC-CAATTAACCCCAT (SEQ ID NO:2) $1^{st}$ round amplification conditions.

One µl of $1^{st}$ round amplification was transferred to the second round amplification reaction mixtures containing primers(R) GST-11 (999-1027) GGGATTTGGGAAA-GAGGGAAAGGTTTTTT (SEQ ID NO:3) (F) GST-12 (1281-1306) ACTAAAAACTCTAAAAACCCCATCCC (SEQ ID NO:4) (R). The location of the primers is indicted according to the GSTP1 sequence (Accession number: M24485). Samples of PCR products were amplified in a ThermoHybaid PX2 thermal cycler under the conditions described in Clark et al.

Agarose gels (2%) were prepared in 1% TAE containing 1 drop ethidium bromide (CLP #5450) per 50 ml of agarose. Five µl of the PCR derived product was mixed with 1 µl of 5× agarose loading buffer and electrophoresed at 125 mA in X1 TAE using a submarine horizontal electrophoresis tank. Markers were the low 100-1000 bp type. Gels were visualised under UV irradiation using the Kodak UVIdoc EDAS 290 system.

Table 2 shows a comparison of the sensitivity of PCR amplification between the HGS method of the invention and the traditional method of Clark et al.

TABLE 2

Sensitivity of PCR-based amplification of the GSTP1 Gene using Human Genetic Signatures (HGS) methodology versus traditional bisulphite amplification procedures (Clark et al, 1994)

| Method | Sensitivity of PCR Amplification | | | |
|---|---|---|---|---|
| | 20,000 | 2,000 | 200 | 20 |
| HGS | Yes | Yes | Yes | Yes |
| traditional | Yes | Yes | No | No |

Effect of pH on Degradation of Bisulphite Treated Genomic DNA

Two µg of LNCaP DNA was digested with 2 units of EcoR1 (Roche #87930626 10 units/µl) according to the manufacturers instructions for 1 hour at 37° C. in a final volume of 20 µl. Eight individual reactions were prepared.

HGS bisulphite treatment of DNA was performed on each of the digests. After treatment, DNA from each individual treatment was resuspended in 20 µl of T/E at either pH 7.0, 8.0, 8.5, 9.0, 9.5, 10.0, 10.5 and 12.5.

The DNA was then incubated using the following methods.

Treatment 1. HGS bisulphite treated genomic DNA was resuspended in buffer solution pH 10.5 and left at 37° C. for 30 minutes then PCR amplified.

Treatment 2. HGS bisulphite treated genomic DNA was resuspended in buffer solution pH 10.5 and left at 37° C. for 120 minutes then PCR amplified.

Treatment 3. HGS bisulphite treated genomic DNA was resuspended in buffer solution pH 10.5 and left at 55° C. for 30 minutes then PCR amplified.

A 1% agarose gel was prepared in 1% TAE containing 1 drop ethidium bromide (CLP #5450) per 50 ml of agarose. Ten µl of the genomic DNA sample was mixed with $\frac{1}{5}^{th}$ volume 5× agarose loading buffer (2 µl) and electrophoresed at 125 mA in X1 TAE using a submarine horizontal electrophoresis tank. Markers were the 100-10,000 range. The gel was visualised and photographed under UV irradiation using the Kodak UVIdoc EDAS 290 system.

PCR Analysis on the Samples

PCR amplification was performed on 1 µl of bisulphite treated DNA resuspended sample DNA as follows.

PCR amplifications were performed in 25 µl reaction mixtures containing 1 µl of bisulphite-treated genomic DNA, using the Promega PCR master mix, 6 ng/µl of each of the primers. The strand-specific nested primers used for amplification of GSTP1 from bisulphite-treated DNA are GST-9 (967-993) TTTGTTGTTTGTTTATTTTTAGGTTT (SEQ ID NO: 1) (F) GST-10 (1307-1332) AACCTMTAC-TACCAATTAACCCCAT (SEQ ID NO: 2) $1^{st}$ round amplification conditions.

One µl of $1^{st}$ round amplification was transferred to the second round amplification reaction mixtures containing primers(R) GST-11 (999-1027) GGGATTTGGGAAA-GAGGGAAAGGTTTTTT (SEQ ID NO: 3) (F) GST-12 (1281-1306) ACTAAAAACTCTAAAAACCCCATCCC (SEQ ID NO: 4) (R). The location of the primers is indicted according to the GSTP1 sequence (Accession number: M24485). Samples PCR products were amplified in a ThermoHybaid PX2 thermal cycler under the conditions described in Clark et al.

Agarose gels (2%) were prepared in 1% TAE containing 1 drop ethidium bromide (CLP #5450) per 50 ml of agarose. Five µl of the PCR derived product was mixed with 1 µl of 5× agarose loading buffer and electrophoresed at 125 mA in X1 TAE using a submarine horizontal electrophoresis tank. Markers were the low 100-1000 bp type. Gels were visualised under UV irradiation using the Kodak UVIdoc EDAS 290 system.

The results are summarized in Table 3. The first point of the results of Table 3 is to demonstrate that when the pH of the bisulphite treated genomic DNA solution is low, then no significant amplification can be detected by standard PCR methods. This is probably due to incomplete de-sulphonation of the bisulphite treated genomic DNA.

The results in Table 3 demonstrate that there is dynamic equilibrium between pH and temperature with regard to the rate of de-sulphonation of the bisulphite treated genomic DNA. If the bisulphite treated genomic DNA is left in low pH solutions, then the rate of de-sulphonation is very slow but can be improved by increasing the temperature of the solution. For example, it may be possible to have the bisulphite treated genomic DNA at pH 7.0, heat it at 72° C., leave it for 48 hours, and then achieve complete de-sulphonation. Likewise, at pH 10.5 the reaction may be finished in 5 minutes at 72° C. Thus, a range of temperatures from room temperature to about 95° C. would be suitable for the present invention. pH ranges from 7.0 to 12.5 and incubation times from about 1 minute to about 96 hours would be suitable. It will be appreciated that various possible combinations of pH, time and temperature would be suitable.

In addition, if the samples were treated with the conventional method, then there would be a large loss of DNA when the bisulphite treated genomic DNA is passed down a size exclusion chromatography column to desalt the solution. It is very likely that at least 50% of the bisulphite treated genomic DNA, if not more, is lost because the conventional columns that are used in the prior art are not designed for single stranded DNA material and there is a large loss. Using the HGS procedure without column purification, the loss by the HGS procedure is miniscule.

TABLE 3

Effect of pH on the degradation of bisulphite treated genomic DNA using the HGS methodology

| | pH of the buffered DNA solution | | | | | | | |
|---|---|---|---|---|---|---|---|---|
| | 7.0 | 8.0 | 8.5 | 9.0 | 9.5 | 10.0 | 10.5 | 12.5 |
| High molecular weight DNA Degraded PCR Product Generation | No | No | No | No | No | No | No | Yes |
| PCR product Treatment 1 | No | No | No | No | No | No | No | Yes |
| PCR product Treatment 2 | ND | ND | ND | ND | ND | Faint | Yes | ND |
| PCR product Treatment 3 | ND | ND | ND | ND | ND | ND | Yes | ND |

Treatment 1. HGS bisulphite treated genomic DNA was resuspended in buffer solution pH 10.5 and left at 37° C. for 30 minutes then PCR amplified.

Treatment 2. HGS bisulphite treated genomic DNA was resuspended in buffer solution pH 10.5 and left at 37° C. for 120 minutes then PCR amplified.

Treatment 3. HGS bisulphite treated genomic DNA was resuspended in buffer solution pH 10.5 and left at 55° C. for 30 minutes then PCR amplified.

Bisulphite Treatment of Various Cell Lines and Tissues

One µg of DNA from the following cell lines and tissue samples were digested with 2 units of EcoR1 (Roche #87930626 10 units/µl) in duplicate according to the manufacturers instructions for 1 hour at 37° C. in a final volume of 20 µl: LNCaP Prostate cancer cell line DNA, MCF-7 Breast cancer cell line DNA, BL-13 Bladder cancer cell line DNA, HepG2 Liver cancer cell line DNA, HeLa cervical cancer cell line DNA, T-cells from purified Patient # 1, and CD34+ cells purified from Patient # 1

HGS bisulphite treatment of DNA was performed on one set of the digests. After treatment, DNA from each individual sample was resuspended in 20 µl of T/E at either pH 10.5 and incubated at 55° C. for 2 hours. Traditional bisulphite treatment of DNA (Clark et al 1994) was performed on the other set in which after the DNA was modified it was resuspended in 20 µl of T/E pH 8.0.

PCR Analysis on the Samples

PCR amplification was performed on 1 µl of both the traditional and HGS bisulphite treated DNA. Six individual genomic loci were analysed for each sample to determine the genomic coverage represented by the HGS and the traditional bisulphite modification methods.

PCR amplifications were performed in 25 µl reaction mixtures containing 1 µl of bisulphite-treated genomic DNA, using the Promega PCR master mix and 6 ng/µl of each of the 1$^{st}$ round gene specific primers. One µl of 1$^{st}$ round amplification was transferred to the second round amplification reaction mixtures containing 2$^{nd}$ round gene specific primers. PCR products were amplified in a ThermoHybaid PX2 thermal cycler under the conditions described in Clark et al.

Two % agarose gels were prepared in 1% TAE containing 1 drop ethidium bromide (CLP #5450) per 50 ml of agarose. A 5 µl aliquot of the PCR derived product was mixed with 1 µl of 5× agarose loading buffer and electrophoresed at 125 mA in X1 TAE using a submarine horizontal electrophoresis tank. Markers were the low 100-1000 bp type. Gels were visualised under UV irradiation using the Kodak UVIdoc EDAS 290 system.

Genomic DNA treated with the HGS bisulphite method was amplified using conventional PCR technologies with primers designed to detect the GSTP1 gene. The results of the comparison between the prior art method and the method according to the present invention are set out in Table 4.

TABLE 4

Whole Genome Amplification efficiency of HGS methodology versus traditional bisulphite amplification Procedures (Clark et al, 1994)

| Tissue | HGS Technology amplification of Gene 1-6 | | | | | | Traditional Bisulphite amplification of Gene 1-6 | | | | | |
|---|---|---|---|---|---|---|---|---|---|---|---|---|
| | 1 | 2 | 3 | 4 | 5 | 6 | 1 | 2 | 3 | 4 | 5 | 6 |
| a | yes | yes | yes | yes | yes | yes | no | no | no | no | no | no |
| b | yes | yes | yes | yes | yes | yes | no | yes | yes | no | no | no |
| c | yes | yes | yes | yes | yes | yes | yes | yes | yes | yes | no | yes |
| d | yes | yes | yes | yes | yes | yes | no | yes | yes | no | no | no |
| e | yes | yes | yes | yes | yes | yes | yes | yes | no | no | yes | yes |
| f | yes | yes | yes | yes | yes | yes | yes | yes | no | no | no | no |

Tissue samples of Table 4 are as follows:
a) LNCaP Prostate cancer cell line DNA
b) MCF-7 Breast cancer cell line DNA
c) HepG2 Liver cancer cell line DNA
d) HeLa cervical cancer cell line DNA
e) T-cells from purified Patient # 1
f) CD34+ cells purified from Patient # 1

Figure 1:
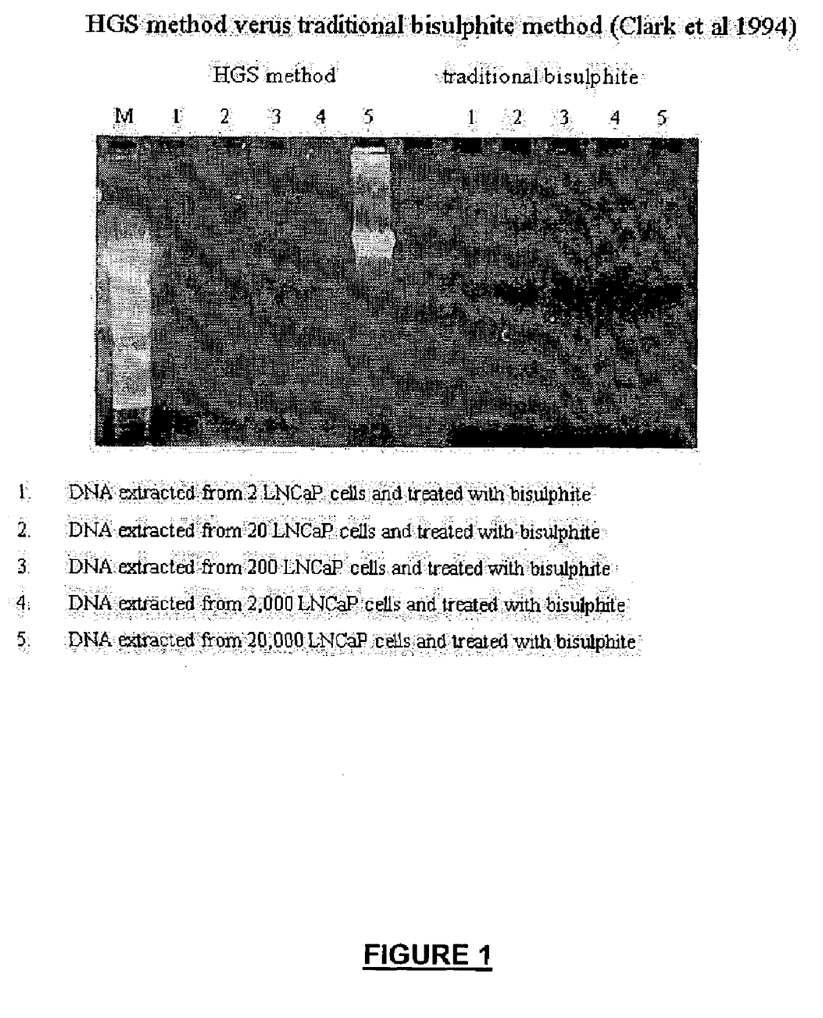
FIG. 1 shows comparison of recovery of bisulphite-treated DNA from various tissue samples between the HGS bisulphite method and traditional bisulphite method (Clark et al., (1994) Nucleic Acids Res. 22:2990-2997). Well#1, DNA extracted from 2 LNCaP cells and treated with bisulphite; Well#2, DNA extracted from 20 LNCaP cells and treated with bisulphite; Well#3, DNA extracted from 200 LNCaP cells and treated with bisulphite; Well#4, DNA extracted from 2,000 LNCaP cells and treated with bisulphite; and Well#5, DNA extracted from 20,000 LNCaP cells and treated with bisulphite. The HGS method is shown on the left (lanes marked 1-5, respectively, as indicated above); the traditional bisulphite method is shown on the right (lanes marked 1-5, respectively, as indicated above).

FIG. 1 shows comparison of recovery of bisulphite-treated DNA from various tissue samples between the HGS bisulphite method and traditional bisulphite method (Clark et al 1994). Well#1.DNA extracted from 2 LNCaP cells and treated with bisulphite, Well#2.DNA extracted from 20 LNCaP cells and treated with bisulphite, Well#3.DNA extracted from 200 LNCaP cells and treated with bisulphite, Well#4.DNA extracted from 2,000 LNCaP cells and treated with bisulphite and Well#5.DNA extracted from 20,000 LNCaP cells and treated with bisulphite As can be seen from FIG. 1, the recovery of DNA using the method according to the present invention is vastly superior to that of the prior art method.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for treating methylated nucleic acid comprising:
   (a) providing an alkali environment to a nucleic acid sample;
   (b) reacting the nucleic acid sample with a bisulphite reagent and incubating the reaction so as to form a treated nucleic acid sample where methylated nucleotides in the nucleic acid sample remain unchanged while unmethylated nucleotides are converted to another form;
   (c) diluting the treated nucleic acid sample so as to reduce salt concentration to a level which will not substantially interfere with a nucleic acid precipitating step;
   (d) precipitating the diluted treated nucleic acid to substantially remove any unwanted reagents or diluents from the treated nucleic acid sample; and
   (e) carrying out de-sulphonation of the precipitated treated nucleic acid at a temperature from 70° C. to 95° C. by adjusting the precipitated treated nucleic acid to a pH of between 10 and less than 12.5 to remove sulphonate groups present on the treated nucleic acid and obtain a nucleic acid sample substantially free of sulphonate groups.

2. The method according to claim 1 wherein more than 50% of the starting nucleic acid in the sample is retained.

3. The method according to claim 2 wherein more than 75% of the starting nucleic acid in the sample is retained.

4. The method according to claim 3 wherein more than 95% of the starting nucleic acid in the sample is retained.

5. The method according to claim 1 further comprising:
   (f) processing or analysing the treated nucleic acid sample.

6. The method according to claim 1 wherein the sample comprises DNA, or the sample comprises RNA, or the sample comprises a combination of both DNA and RNA.

7. The method according to claim 1 wherein the sample is prepared from a tissue, organ, cell, microorganism, biological sample, or environmental sample.

8. The method according to claim 7 wherein the tissue or organ is selected from the group consisting of brain, colon, urogenital, lung, renal, hematopoietic, breast, thymus, testis, ovary, uterus, and mixtures thereof.

9. The method according to claim 7 wherein the microorganism is selected from the group consisting of bacteria, virus, fungi, protozoan, viroid, and mixtures thereof.

10. The method according to claim 7 wherein the biological sample is selected from the group consisting of blood, urine, faeces, semen, cerebrospinal fluid, lavage, cells or tissue from brain, colon, urogenital, lung, renal, hematopoietic, breast, thymus, testis, ovary or uterus, tissues from embryonic or extra-embryonic lineages, environmental samples, plants, microorganisms, bacteria, intracellular parasites, viruses, fungi, protozoa, and viroids.

11. The method according to claim 1 carried out in a reaction vessel.

12. The method according to claim 11 wherein the reaction vessel is selected from the group consisting of a tube, plate, capillary tube, well, centrifuge tube, microfuge tube, slide, coverslip, and surface.

13. The method according to claim 1 wherein the bisulphite reagent is sodium metabisulphite.

14. The method according to claim 1 wherein the alkali environment is provided to the sample by adding an alkali.

15. The method according to claim 14 wherein the alkali is NaOH, KOH, or any compound providing hydroxyl groups.

16. The method according to claim 1 wherein the step (a) is carried out in the presence of an additive capable of enhancing the bisulphite reaction.

17. The method according to claim 16 wherein the additive is selected from the group consisting of quinol, urea, methoxyamine, and mixtures thereof.

18. The method according to claim 1 wherein the step (b) results in methylated cytosines in the nucleic acid sample remaining unchanged while unmethylated cytosines are converted to uracils.

19. The method according to claim 1 wherein the dilution step (c) is carried out using water to reduce salt concentration to below 0.5 M.

20. The method according to claim 1 wherein the precipitation is carried out using an alcohol precipitating agent.

21. The method according to claim 20 wherein the alcohol precipitating agent is selected from the group consisting of isopropanol, ethanol, butanol, methanol, and mixtures thereof.

22. The method according to claim 21 wherein the alcohol is isopropanol.

23. The method according to claim 1 wherein the de-sulphonation step (e) is carried out by adjusting the pH of the precipitated treated nucleic acid with a buffer or alkali reagent.

24. The method according to claim 1 wherein the pH is adjusted to about 10.5.

25. A method for treating methylated nucleic acid comprising:
   (a) providing an alkali environment to a nucleic acid sample by adding NaOH;
   (b) reacting the nucleic acid sample with sodium metabisulphite and incubating the reaction so as to form a treated nucleic acid sample where methylated nucleotides in the nucleic acid sample remain unchanged while unmethylated nucleotides are converted to another form;
   (c) diluting the treated nucleic acid sample with water so as to reduce salt concentration to a level below 0.5 M;
   (d) precipitating the diluted treated nucleic acid with isopropanol to substantially remove any unwanted reagents or diluents from the vessel; and
   (e) carrying out de-sulphonation of the precipitated treated nucleic acid at a temperature from 70° C. to 95° C. by adjusting the precipitated treated nucleic acid to about pH 10.5 with a buffer or alkali reagent so as to remove sulphonate groups present on the treated nucleic acid so as to obtain a nucleic acid sample substantially free of sulphonate groups, wherein more than 50% of the starting nucleic acid in the sample is retained.

26. The method according to claim 25 carried out in one vessel.

27. A method for treating methylated nucleic acid, comprising:
   (a) denaturing a nucleic acid;
   (b) incubating the nucleic acid with a bisulphite reagent, thereby modifying methylated nucleotides with sulphonate groups;
   (c) diluting the modified nucleic acid;
   (d) precipitating the modified nucleic acid; and
   (e) reacting the modified nucleic acid at a temperature from 70° C. to 95° C. to remove sulphonate groups by adjusting the precipitated treated nucleic acid to about pH 10.5 with a buffer or alkali reagent.

28. The method of claim 27, wherein the nucleic acid is denatured with alkali.

29. The method according to claim 25 wherein the sample comprises DNA, or the sample comprises RNA, or the sample comprises both DNA and RNA.

30. The method according to claim 27 wherein the nucleic acid is DNA, or the nucleic acid is RNA, or the nucleic acid comprises both DNA and RNA.

* * * * *